United States Patent
Matsushita et al.

(10) Patent No.: US 8,609,918 B2
(45) Date of Patent: *Dec. 17, 2013

(54) METHOD OF PRODUCING PARA-SUBSTITUTED AROMATIC HYDROCARBON

(75) Inventors: Koichi Matsushita, Toda (JP); Chikanori Nakaoka, Toda (JP); Naoharu Igarashi, Toda (JP); Makoto Oyamada, Toda (JP)

(73) Assignee: JX Nippon Oil & Energy Corporation, Tokyo (JP)

( * ) Notice: Subject to any disclaimer, the term of this patent is extended or adjusted under 35 U.S.C. 154(b) by 207 days.

This patent is subject to a terminal disclaimer.

(21) Appl. No.: 12/922,510

(22) PCT Filed: Mar. 26, 2009

(86) PCT No.: PCT/JP2009/056095
§ 371 (c)(1),
(2), (4) Date: Sep. 14, 2010

(87) PCT Pub. No.: WO2009/119725
PCT Pub. Date: Oct. 1, 2009

(65) Prior Publication Data
US 2011/0009682 A1    Jan. 13, 2011

(30) Foreign Application Priority Data

| Mar. 27, 2008 | (JP) | 2008-083574 |
| Mar. 27, 2008 | (JP) | 2008-083603 |
| Mar. 27, 2008 | (JP) | 2008-083781 |
| Mar. 27, 2008 | (JP) | 2008-084446 |

(51) Int. Cl.
C07C 2/66    (2006.01)
C07C 5/22    (2006.01)

(52) U.S. Cl.
USPC .................. 585/467; 585/477; 585/828

(58) Field of Classification Search
USPC ............................ 585/467, 477, 828
See application file for complete search history.

(56) References Cited

U.S. PATENT DOCUMENTS

| 4,465,886 A * | 8/1984 | Rodewald ............... 585/467 |
| 7,122,496 B2 * | 10/2006 | Doyle et al. .............. 502/71 |

FOREIGN PATENT DOCUMENTS

| CN | 1224408 A | 7/1999 |
| JP | A-61-221137 | 10/1986 |
| JP | A-64-90140 | 4/1989 |
| JP | A-8-509907 | 10/1996 |
| JP | A-2001-504084 | 3/2001 |
| JP | A-2002-515054 | 5/2002 |
| JP | A-2002-302461 | 10/2002 |
| JP | A-2003-62466 | 3/2003 |
| JP | A-2007-517030 | 6/2007 |
| WO | WO 2005/068406 A1 | 7/2005 |

OTHER PUBLICATIONS

International Search Report for International Patent Application No. PCT/JP2009/056095, mailed on Jun. 16, 2009 (w/ English translation).
Jul. 30, 2013 Notification of Reasons for Refusal issued in Japanese Application No. 2010-505766 with English-language translation.
Nov. 29, 2012 First Office Action issued in Chinese Application No. 200980110882.4 with English-language translation.

* cited by examiner

*Primary Examiner* — Thuan D Dang
(74) *Attorney, Agent, or Firm* — Oliff & Berridge, PLC (57) ABSTRACT

This invention relates to a method of efficiently producing a high-purity para-substituted aromatic hydrocarbon while suppressing caulking without requiring isomerization-adsorption separation steps, and more particularly to a method of producing a para-substituted aromatic hydrocarbon, characterized in that a methylating agent and an aromatic hydrocarbon are reacted in the presence of a catalyst formed by coating MFI type zeolite having a particle size of not more than 100 μm with a crystalline silicate.

5 Claims, 2 Drawing Sheets

METHOD OF PRODUCING PARA-SUBSTITUTED AROMATIC HYDROCARBON

TECHNICAL FIELD

This invention relates to a method of producing a para-substituted aromatic hydrocarbon, and more particularly to a method of simply and efficiently producing para-di-substituted alkylbenzens with a high purity.

RELATED ART

Among aromatic compounds, xylenes are very important compounds as a starting material for the production of terephthalic acid, isophthalic acid, orthophthalic acid or the like being as a starting material of a polyester. These xylenes are produced, for example, by transalkylation, disproportionation or the like of toluene. However, p-xylene, o-xylene and m-xylene are existent in the product as a structural isomer. Since terephthalic acid obtained by oxidizing p-xylene is used as a main starting material of polyethylene terephthalate and phthalic anhydride made from o-xylene is used as a starting material for a plasticizer or the like and isophthalic acid made from m-xylene is used as a main starting material for an unsaturated polyester or the like, it is desired to develop a method wherein these structural isomers are separated from the product efficiently.

However, there is substantially no difference in the boiling point among p-xylene (boiling point 138° C.), o-xylene (boiling point 144° C.) and m-xylene (boiling point 139° C.), so that it is difficult to separate these isomers by the usual distillation method. On the other hand, as the method of separating these isomers, there are a super-cold separation method wherein a xylene mixture including p-, o- and m-isomers are rectified and then p-xylene having a higher melting point is crystallized and separated by cooling, a method wherein p-xylene is separated by adsorption using a zeolite-series adsorbent having a sieving action, and so on.

In the method of selectively separating p-xylene through the super-cold separation, the crystallization by cooling should be conducted after the rectification of the xylene mixture containing structural isomers, so that there are problems that the process becomes multi-stages and complicated and the production cost is increased by the rectification and the crystallization by cooling, and so on. Instead of this method, therefore, is most widely conducted the adsorption separation method at the present day. The latter method is a system wherein the staring xylene mixture is moved through an adsorption tower filled with the adsorbent, during which paraxylene having a strong adsorbing force as compared with the other isomers is adsorbed and separated from the other isomers. Then, paraxylene is removed out from the tower with the adsorbent and then desorbed and separated from the desorbing solution by distillation. As an actual process are mentioned PARE method by UOP and AROMAX method by Toray. Although this adsorption separation method is high in the recovery and purity of paraxylene as compared with the other separation method, the adsorption and desorption are sequentially repeated by the adsorption tower comprising artificial fluidized beds of several tens stages, so that the desorbing agent for removing paraxylene from the adsorbent is required to be removed separately, and hence the method is never good in the operation efficiency when the purity of paraxylene is increased.

On the contrary, it is attempted to improve the efficiency in the adsorption separation method of paraxylene. For instance, Japanese Patent No. 2647152 discloses a method wherein ZSM-5 zeolite having a high silica/alumina ratio is used as an adsorbent and a light paraffin is used as a desorbing agent.

Further, JP-A-2002-302461 presents a case of applying a membrane separation method as the separation method. In this case, the desorbing agent as in the conventional adsorption separation method is useless, but the separation rate drops down but also the production of the target product reduces.

Aromatic hydrocarbons with a carbon number of 8 such as xylenes and the like are existent at about 20 volume % in a catalytic reformed oil obtained from a catalytic reforming process, so that they are also produced by utilizing disproportionation of toluene or transalkylation between toluene and an aromatic hydrocarbon with a carbon number of 9. However, since both the disproportionation and the transalkylation are a reaction associated with the movement of methyl group, caulking occurs easily. In order to suppress the deterioration of the catalyst due to the caulking, therefore, the reaction should be carried out under pressure of hydrogen.

On the other hand, the aromatic hydrocarbons with a carbon number of 8 are also produced by methylation of toluene. Further, it is attempted to selectively conduct the methylation of toluene to selectively produce paraxylene. For instance, as a method of conducting the separation while giving separation function to the catalyst to conduct the reaction is disclosed a zeolite-bonded zeolite catalyst comprised of the first zeolite crystal having a catalytic activity and the second zeolite crystal having a molecular sieving action in JP-A-2001-504084. In the zeolite-bonded zeolite catalyst disclosed in JP-A-2001-504084, however, the second zeolite crystal having a molecular sieving action forms a continuously phase matrix or a bridge, so that a ratio of the first zeolite crystal having a catalytic activity occupied in the zeolite-bonded zeolite catalyst becomes small, which causes the deterioration of the catalytic activity, but also when the second zeolite crystal having a molecular sieving action forms a continuously phase matrix, permeation resistance of molecule selected becomes too large and the molecular sieving action tends to be deteriorated. Further, a binder (carrier) for holding the shape is not used and the second zeolite crystal assumes a role as a binder (carrier), so that there is obtained a zeolite-bonded zeolite catalyst in which the first zeolite crystal is aggregated or lumped by the second zeolite crystal once. The segregated or lumped catalyst is pulverized in use, but the second zeolite crystal is peeled by the pulverization to produce an exposed portion of the first zeolite crystal, which causes the deterioration of the molecular sieving action.

In JP-A-2003-62466 is disclosed a method of coating solid acid catalyst particles with a zeolite crystal having a molecular sieving action. In this method, however, the average particle size of the catalyst particles is 0.3-3.0 mm, so that a reaction site required for the target reaction, i.e. a specific surface area of the catalyst is very small. Therefore, this method is insufficient in the reaction efficiency and is not so high in the toluene conversion and the selectivity of paraxylene and can not be used industrially.

Turning attention to a methylating agent, JP-A-2007-517030 discloses a method of optimizing a catalyst for the purpose of improving a utility factor of methanol. However, this method is not so high in the toluene conversion and the selectivity of paraxylene and can not be used industrially.

As the reaction of methanol is known so-called MTO (Methanol To Olefin) reaction or MTG (Methanol To Gasoline) reaction wherein methanol is converted into olefin or aromatic hydrocarbon on a solid acid catalyst such as MFI zeolite or alumina as presented in Petroleum Purification Process, page 231 edited by Institute of Petroleum. When methanol is used as a methylating agent, olefin or aromatic hydrocarbon is produced by methanol-methanol reaction to cause caulking, which has a problem that the service life of the catalyst becomes short.

DISCLOSURE OF THE INVENTION

In the conventional technique as mentioned above, the para-substituted aromatic hydrocarbons of a high purity can not be produced efficiently without passing through isomerization and adsorption separation steps. If the isomerization and adsorption separation steps are utilized, there is a is problem in the operation efficiency. Also, when methanol is used as the methylating agent, olefin or aromatic hydrocarbon causing the caulking is easily by-produced by methanol-methanol reaction, which has a problem that the service life of the catalyst becomes short.

In light of the above situation, it is the first object of the invention to provide a method wherein a para-substituted aromatic hydrocarbon, particularly paraxylene with a high purity is produced efficiently by using a catalyst having a molecular sieve action and being excellent in the catalyst activity to suppress caulking without requiring isomerization-adsorption separation steps.

The inventors have made various studies and found an epoch-making method of producing a para-substituted aromatic hydrocarbon in which the separation is made easy by selecting an optimum catalyst to alkylation reaction of aromatic hydrocarbon and impurities are not contained substantially. In the invention, only an isomer of a specified structure among products formed inside of catalyst particles can be selectively passed through a crystalline silicate membrane having a molecular sieve action to enhance the selectivity of the isomer of the specified structure, or inversely only the isomer of the specified structure can be selectively penetrated into the inside of the catalyst particles having an catalytic activity to cause selective (peculiar) reaction inside the catalyst particles. As a result, the invention can produce a para-substituted aromatic hydrocarbon of a high purity efficiently and stably over a log period.

That is the production method of para-substituted aromatic hydrocarbon according to the invention is characterized in that a methylating agent and an aromatic hydrocarbon are reacted in the presence of a catalyst formed by coating MFI type zeolite having a particle size of not more than 100 μm with a crystalline silicate.

In a preferable embodiment of the production method of para-substituted aromatic hydrocarbon according to the invention, the methylating agent is at least one selected from the group consisting of methanol and dimethyl ether.

In another preferable embodiment of the production method of para-substituted aromatic hydrocarbon according to the invention, a conversion of the aromatic hydrocarbon is not less than 30 mol %, and paraxylene among aromatic hydrocarbons with a carbon number of 8 included in a reaction product is not less than 95 mol %.

In the other preferable embodiment of the production method of para-substituted aromatic hydrocarbon according to the invention, a para-substituted aromatic hydrocarbon of a high purity is obtained from the reaction product by distillation without isomerization-adsorption separation.

Since individual catalyst particles of MFI type zeolite used in the invention are coated with the crystalline silicate membrane having a molecular sieve action over their surfaces, an isomer of a specified structure can be selectively produced by utilizing the molecular sieve action. Especially, ZSM-5 of MFI structure is coated with a silicalite membrane having the same structure, whereby the shape selectivity of para-isomer of dialkylbenzene can be given to the catalyst particles. As seen from the above, para-substituted aromatic hydrocarbons including an industrially useful paraxylene can be produced selectively.

As previously mentioned, according to the conventional technique, paraxylene with a high purity has been produced by subjecting an aromatic hydrocarbon in a catalytic reformed oil obtained through catalytic reforming process to multistage and large energy consumed steps of disproportionation or transalkylation, isomerization and/or dealkylation, and further adsorption separation. Therefore, paraxylene of a high purity could not be produced efficiently by a mild method being less in the energy consumption.

It is, therefore, the second object of the invention to provide a method of producing paraxylene in a low cost efficiently wherein an aromatic hydrocarbon with a carbon number of 7 is methylated under mild reaction conditions by using a catalyst having a molecular sieve action (or shape selectivity) and an excellent catalytic activity to produce paraxylene of a high purity efficiently, whereas an aromatic hydrocarbon with a carbon number of 8 is isomerized and adsorption-separated to produce paraxylene, whereby it is possible to utilize both aromatic hydrocarbons with carbon number of 7 and 8 in a catalytic reformed oil and reduce a working ratio of isomerization-adsorption separation apparatus.

The inventors have made various studies and found an epoch-making method of producing paraxylene in which the separation is made easy by selecting an optimum catalyst to methylation reaction of aromatic hydrocarbon and impurities are not contained substantially. In the invention, only paraxylene formed inside the catalyst particles can be selectively passed through a silicalite membrane having a molecular sieve action to enhance the selectivity of paraxylene. Therefore, according to the invention, paraxylene of a high purity can be produced from aromatic hydrocarbon efficiently. Also, paraxylene is produced by isomerization and/or adsorption separation, whereby aromatic hydrocarbon with a carbon number of 8 can be utilized as a starting material for paraxylene. In this case, paraxylene produced by the isomerization and/or adsorption separation is mixed with the high-purity paraxylene produced by the methylation of the aromatic hydrocarbon to form a final product, whereby it is made possible to reduce the purity of paraxylene produced by the isomerization and/or adsorption separation, and hence the working ratio of isomerization-adsorption separation apparatus can be reduced to reduce the production cost as a whole.

That is, the production method of paraxylene according to the invention is characterized by comprising:

a first step of reacting a methylating agent and an aromatic hydrocarbon in the presence of a catalyst formed by coating MFI type zeolite having a particle size of not more than 100 μm with a crystalline silicate to produce paraxylene;

a second step of isomerizing and/or adsorption-separating an aromatic hydrocarbon with a carbon number of 8 to produce paraxylene; and a third step of mixing paraxylene obtained in the first step with paraxylene obtained in the second step.

Since individual catalyst particles of MFI type zeolite used in the production method of paraxylene according to the invention are coated with the crystalline silicate membrane having a molecular sieve action over their surfaces, paraxylene can be selectively produced by utilizing the molecular sieve action. Especially, ZSM-5 of MFI structure is coated with a silicalite membrane having the same structure, whereby the shape selectivity of paraxylene can be given to the catalyst particles. Therefore, paraxylene with a very high purity can be produced in the first step. Since the purity of paraxylene obtained in the first step is very high, even if the burden of the second step being high in the running cost is reduced to lower the purity of paraxylene, the mixing ratio of paraxylene from the first step to paraxylene from the second step can be properly adjusted to attain a target purity of paraxylene obtained in the third step.

BEST MODE FOR CARRYING OUT THE INVENTION

[Catalyst]

In the production method of a para-substituted aromatic hydrocarbon according to the invention is used a catalyst formed by coating MFI type zeolite having a particle size of not more than 100 μm with a crystalline silicate. The zeolite of MFI structure used as a nucleus of the catalyst is excellent in the catalyst performance to the reaction of producing a para-substituted aromatic hydrocarbon by reacting a methylating agent with an aromatic hydrocarbon. As the MFI type zeolite are particularly preferable ZSM-5 and SAPO-34. Since the pore size in these zeolites is 0.5-0.6 nm and the same as in a minor axis of paraxylene molecule, paraxylene can be distinguished from orthoxylene and methaxylene having a molecular size slightly larger than that of paraxylene, so that the zeolite is particularly effective when the target para-substituted aromatic hydrocarbon is paraxylene.

The MFI type zeolite forming the nucleus of the catalyst has a particle size of not more than 100 μm. When the particle size of the MFI type zeolite exceeds 100 μm, a reaction site required for the objective reaction or a specific surface area of the catalyst becomes very small and the reaction efficiency lowers and the diffusion resistance becomes large, and hence the conversion of the starting aromatic hydrocarbon and para-selectivity become low, so that the particle size exceeding the given value can not be used industrially. Moreover, as the particle size of the MFI type zeolite used becomes small, the influence of diffusion inside the pores can be desirably reduced, so that it is preferably not more than 50 μm, more preferably not more than 20 μm, particularly preferably not more than 10 μm. The particle size can be measured by a particle size distribution meter, a scanning type electron microscope (SEM) or the like.

Also, the silica/alumina ratio in the MFI zeolite is preferably not less than 30 but not more than 2000, more preferably not less than 50 but not more than 1000. When the silica/alumina ratio is less than 30, it is difficult to stably hold the MFI structure, while when it exceeds 2000, an amount of an acid as an alkylation active point becomes undesirably low.

The catalyst used in the invention is formed by coating the MFI type zeolite with a crystalline silicate, and the crystalline silicate develops the molecular sieve action. The crystalline silicate membrane (zeolite membrane) having the molecular sieve action is preferable to have a structure similar to the MFI type zeolite as the nucleus and continuous pores. Moreover, the crystalline silicate is desirable to be inactive to alkylation reaction, and is particularly preferable to be pure silica-zeolite containing no alumina (silicalite). Since silicalite has substantially no acid point, it is particularly preferable because the surface after the coating is inactivated to alkylation reaction. Moreover, silicon in the crystalline silicate may be partially replaced with another element such as gallium, germanium, phosphorus, boron or the like. Even in the latter case, it is important to maintain the inactive state of the surface.

The weight of the crystalline silicate based on 100 parts of the MFI type zeolite as a nucleus is preferably not less than 10 parts, more preferably not less than 20 parts, and is preferably not more than 100 parts, more preferably not more than 70 parts. When the crystalline silicate is less than 10 parts by weight based on 100 parts by weight of the MFI type zeolite, the molecular sieve action of the crystalline silicate can not be developed sufficiently, while when it exceeds 100 parts by weight, the ratio of the MFI type zeolite in the catalyst is too low, resulting in the deterioration of the catalytic activity but also the resistance of the treating body such as starting material, product and the like passing through the crystalline silicate membrane may become too large. in this case, the thickness of the crystalline silicate is preferably not less than 0.001 μm, more preferably not less than 0.005 μm, particularly not less than 0.01 μm but is preferably not more than 50 μm, more preferably not more than 10 μm, particularly not more than 0.5 μm. When the thickness of the crystalline silicate is less than 0.001 μm, the molecular sieve action of the crystalline silicate membrane can not be developed sufficiently, while when it exceeds 50 μm, the thickness of the crystalline silicate is too thick and the resistance of the treating body such as starting material, product and the like passing through the crystalline silicate membrane may become too large.

In the invention, the method of coating the whole of particle surfaces of the MFI type zeolite with the crystalline silicate membrane is not particularly limited, but the conventional method of preparing zeolite membrane such as hydrothermal synthesis method or the like can be used. For instance, a silica source such as sodium silicate, colloidal silica or the like and a mineralizer such as hydroxide of an alkali metal or an alkaline earth metal or the like are first dissolved in water in accordance with the composition of the target crystalline silicate membrane to prepare a sol for the formation of the crystalline silicate membrane. Then, individual particles of the MFI type zeolite are immersed in the sol for the formation of the crystalline silicate membrane or the sol for the formation of the crystalline silicate membrane is applied onto individual particles of the MFI type zeolite to treat the whole surface of the individual particles of the MFI type zeolite with the sol for the formation of the crystalline silicate membrane. Thereafter, hydrothermal treatment is carried out to form the crystalline silicate membrane on the whole surface of the individual particles of the MFI type zeolite. The hydrothermal treatment can be conducted by immersing the particles of the MFI type zeolite treated with the sol for the formation of the crystalline silicate membrane in hot water or in hot water inside an autoclave, or leaving to stand in heated steam. Also, the hydrothermal treatment may be conducted at a state of immersing the particles of the MFI type zeolite in the sol for the formation of the crystalline silicate membrane. In the latter case, an autoclave including the particles of the MFI type zeolite and the sol for the formation of the crystalline silicate membrane may be directly heated in an oven. The hydrothermal treatment is carried out at a temperature of preferably not lower than 120° C., more preferably not lower than 150° C. but preferably not higher than 250° C., more preferably not higher than 200° for a time of preferably not less than 0.5 hour, more preferably not less than 1 hour but preferably not more than 48 hours, more preferably not more than 36 hours. After the hydrothermal treatment, the particles of the MFI type zeolite are taken out and dried and further subjected to a heat treatment to sinter the crystalline silicate membrane. The sintering may be carried out by raising a temperature at a rising rate of 0.1-10° C./min, if necessary, and heating at a temperature of 500° C. to 700° C. for 2-10 hours.

In the invention, the catalyst is typically filled in a reactor to form a catalyst layer. The void fraction of the catalyst layer can be indicated by the filling density of the catalyst. In the production method of the invention, the catalyst filling density is preferably not less than 0.10 g/ml but not more than 0.60 g/ml, more preferably not less than 0.20 g/ml but not more than 0.57 g/ml, further preferably not less than 0.30 g/ml but not more than 0.55 g/ml. When the catalyst filling density is not less than 0.10 g/ml but not more than 0.6 g/ml, it is possible to suppress progression of microscopically excessive reaction as far as possible and the deterioration of the catalyst due to caulking or the like can be controlled. Moreover, the catalyst filling density in the invention can be calculated by the measurement of a tapped density. When the catalyst filling density exceeds 0.60 g/ml, the microscopically excessive reaction proceeds and the catalyst may be deteriorated due to the caulking or the like, so that the catalyst filling density is preferable to be not more than 0.60 g/ml. Also, when the catalyst filling density is less than 0.10 g/ml, the alkylation of the aromatic hydrocarbon does not proceed sufficiently, and the conversion of the aromatic hydrocarbon may be lowered, so that the catalyst filling density is preferable to be not less than 0.10 g/ml.

As previously mentioned, when methanol is used as a methylating agent, olefin and aromatic hydrocarbon resulting in the caulking are easily by-produced by methanol-methanol reaction, so that there is a problem that the service life of the catalyst becomes short. However, such a problem can be solved surely when the catalyst filling density is not less than 0.10 g/ml but not more than 0.6 g/ml.

In order to maintain the above catalyst filling density can be applied the existing granulation method. Concretely, press molding method, extrusion molding method, tumbling granulation method, spray drying method and the like can be applied. When the particle size of the catalyst is determined, it is common to select the particle size of the catalyst by a size of a reactor, particularly an inner diameter of the reactor. In case of sphere, the diameter of the catalyst is preferable to be not less than 1 mm but not more than 20 mm, and in case of cylinder, it is preferable that the length of the catalyst is not less than 1 mm but not more than 20 mm and the diameter of the catalyst is not less than 0.5 mm but not more than 10 mm.

[Alkylation of Aromatic Hydrocarbon]

In the production method of para-substituted aromatic hydrocarbon according to the invention, a methylating agent and an aromatic hydrocarbon are reacted (concretely alkylated) in the presence of the aforementioned catalyst to selectively produce a para-substituted aromatic hydrocarbon. The term "para-substituted aromatic hydrocarbon" used herein means an aromatic hydrocarbon having two alkyl substituents on its aromatic ring in which one of the substituents is located in a para site to the other substituent.

As the starting aromatic hydrocarbon are mentioned benzene and an alkylbenzene. Moreover, the starting aromatic hydrocarbom may contain am aromatic hydrocarbon other than benzene and the alkylbenzene. Especially, a preferable embodiment of the invention is the selective production of p-xylene using a starting material including toluene. Because p-xylene is a starting material of terephthalic acid being a starting material of an industrially useful polyethylene terephthalate resin, and is an industrially very important starting material.

As the alkylbenzene usable as the starting material is selected a monoalkylbenzene as a monosubstitution product of benzene. For example, toluene being a simplest structure of the monoalkylbenzene is a preferable embodiment of the invention. When the monoalkylbenzene is used as the starting aromatic hydrocarbon, dialkylbenzen as a disubstitution product is obtained by one-stage alkylation reaction. On the other hand, when benzene is used as the starting aromatic hydrocarbon, dialkylbenzene as a disubstitution product is obtained by two-stage alkylation reaction.

In the invention, the methylating agent for the aromatic hydrocarbon is not particularly limited, and well-known methylating agents can be used. As the methylating agent are mentioned, for example, methanol, dimethyl ether (DME), methyl chloride, methyl bromide, dimethyl sulfate and the like. Among them, methanol and dimethyl ether are preferable.

In the conventional alkylation reaction of the aromatic hydrocarbon, methanol is frequently used as the methylating agent. However, since methanol is consumed under conditions for alkylation reaction by converting to light paraffins or light olefins with a carbon number of about 2-5 through reaction of methanol itself or further aromatic hydrocarbon based on polymerization of olefin, it is required to charge methanol in an amount larger than an amount theoretically required for the alkylation reaction. Also, when methanol is used as the methylating agent, caulking is caused due to the formation of olefin and the like to deteriorate the catalyst, so that it is required to take a countermeasure therefor. On the contrary, when dimethyl ether is used as the methylating agent, it is possible to suppress by-production of olefin resulting in the caulking and aromatic hydrocarbon based on the polymerization of olefin because the methylating agent is consumed efficiently. Furthermore, the use of methanol as a starting material is not preferable because there is a fear of badly affecting the reaction such as poisoning of an active point through by-produced water or the like. Therefore, dimethyl ether (DME) being less in the ratio of water produced per molecule is particularly preferable as the methylating agent.

As dimethylether may be used commercially available ones, but the starting material may be, for example, dimethyl ether produced by dehydration reaction of methanol or dimethyl ether produced from a synthesis gas being a mixed gas of hydrogen and carbon monoxide. That is, the production method of the invention may be comprised of a step (A) of producing dimethyl ether from methanol or synthesis gas and a step (B) of producing a para-substituted aromatic hydrocarbon from dimethyl ether and an aromatic hydrocarbon. In this case, the step (a) can be conducted according to the known method. For example, the production of DME through dehydration reaction of methanol can be conducted according to the known method at a reaction temperature of 200-350° C. in the presence of a solid acid catalyst.

The ratio of the methylating agent to the aromatic hydrocarbon in the alkylation reaction as a molar ratio is preferably 5/1-1/10, more preferably 2/1-1/5, particularly 1/1-1/2. When the amount of the methylating agent to the aromatic hydrocarbon is extremely large, there is a possibility that the undesired reaction between the mutual methylating agents proceeds to cause caulking resulting in the deterioration of the catalyst. On the other hand, when the amount of the methylating agent to the aromatic hydrocarbon is extremely small, there is a possibility that the alkylation to aromatic hydrocarbon does not proceed but also when an alkylbenzene is used as the aromatic hydrocarbon, the deterioration of the catalyst is caused associated with the disproportionation or dealkylation reaction of the alkylbenzene. Moreover, as an impurity capable of existing in the starting aromatic hydrocarbon and the methylating agent are mentioned water, olefin, sulfur compound and nitrogen compound, but these impurities are preferable to be less. As a preferable content of the impurity, water is not more than 200 ppm by weight, more preferably not more than 100 ppm by weight, and the olefin is not more than 1 weight %, more preferably not more than 0.5 weight %, and the sulfur and nitrogen compounds are not more than 1 ppm by weight, more preferably not more than 0.1 ppm by weight.

In the production method of the invention, when methanol is used as the methylating agent, the molar ratio of the methanol to the aromatic hydrocarbon is preferably not less than 0.45 but not more than 4.0, more preferably not less than 0.47 but not more than 3.0, further preferably not less than 0.5 but not more than 1.0. When the molar ratio of methanol to the aromatic hydrocarbon exceeds 4.0, there is a possibility that the undesired reaction between the mutual methanols proceeds to cause caulking resulting in the deterioration of the catalyst, so that the molar ratio of methanol to the aromatic hydrocarbon is preferable to be not more than 4.0. Also, when the molar ratio of methanol to the aromatic hydrocarbon is less than 0.45, there is a possibility that the alkylation to aromatic hydrocarbon hardly proceeds but also when an alkylbenzene is used as the aromatic hydrocarbon, the deterioration of the catalyst is caused associated with the disproportionation or dealkylation reaction of the alkylbenzene, so that the molar ratio of methanol to the aromatic hydrocarbon is preferable to be not less than 0.45.

It is desirable that the alkylation reaction is carried out by feeding the starting aromatic hydrocarbon at a spatial velocity of not less than 0.01/hr, preferably not less than 0.1/hr but not more than 10/hr, more preferably 5/hr to bring in contact with the above catalyst. The conditions of the alkylation reaction are not particularly limited, but the reaction temperature is preferably not lower than 200° C., more preferably not lower than 230° C., further preferably not lower than 250° C., particularly not lower than 260° C. but preferably not higher than 500° C., more preferably not higher than 420° C., further preferably not higher than 360° C., and the pressure is preferably not less than atmospheric pressure, more preferably not less than 0.1 MPaG, particularly not less than 0.5 MPaG but preferably not more than 10 MPaG, more preferably not more than 5 MPaG. In the alkylation reaction, an inert gas such as nitrogen or helium or a hydrogen gas for suppressing the caulking may be circulated or flown under a pressure. Moreover, when the reaction temperature is too low, the activation of the methylating agent is insufficient and an active point is poisoned through water produced by the reaction, and hence the conversion of the starting aromatic hydrocarbon is low, while when the reaction temperature is too high, a greater amount of energy is consumed but also the catalyst life tends to become short.

When the alkylation reaction of the aromatic hydrocarbon by the methylating agent proceeds in the presence of the catalyst, it is assumed to form a para-substituted aromatic hydrocarbon as a target product as well as an ortho-substituted aromatic hydrocarbon and a metha-substituted aromatic hydrocarbon as a structural isomer, a mono-substituted aromatic hydrocarbon in which the carbon number in the substituent is increased as compared with the starting aromatic hydrocarbon, an unreacted aromatic hydrocarbon, an aromatic hydrocarbon having 3 or more substituents associated with the proceeding of the methylation, and so on. Among them, it is preferable that the component ratio of the para-substituted aromatic hydrocarbon becomes higher. As an indication of para-selectivity in the reaction, when an aromatic hydrocarbon with a carbon number of 8 in the product is taken into account, the selectivity of paraxylene among aromatic hydrocarbons with a carbon number of 8 is preferably not less than 95 mol %, more preferably not less than 99.7 mol %, further preferably not less than 99.8 mol %, particularly not less than 99.9 mol % at the first stage of the reaction. Since the selectivity is high, it is possible to produce a high-purity para-substituted aromatic hydrocarbon only by a simple distillation without further subjecting the reaction product to isomerization-adsorption separation.

On the other hand, the conversion of the starting aromatic hydrocarbon is preferable to become higher. The conversion of the starting aromatic hydrocarbon is largely dependent upon the reaction temperature and the ratio of the methylating agent, but is preferably not less than 30 mol %, more preferably not less than 50 mol %, particularly not less than 70 mol % assuming the actual process. When the conversion of the starting aromatic hydrocarbon is low, it is required to return the unreacted aromatic hydrocarbon to the starting line for conducting the reaction again, and hence there is a demerit that the production efficiency is largely lowered.

Since the aromatic hydrocarbons having 3 or more substituents are easily formed under the reaction condition that the ratio of the methylating agent becomes higher, it is preferable that the molar ratio of the methylating agent to the aromatic hydrocarbon is not so high as previously mentioned. The content in total of the aromatic hydrocarbons having 3 or more substituents in the reaction product is preferably not more than 5 mol %, more preferably not more than 1 mol %, particularly not more than 0.1 mol %. When the aromatic hydrocarbons having 3 or more substituents are large, a greater amount of energy is required for the separation such as distillation or the like, so that the forming amount is particularly preferable to be not more than 0.1 mol %.

The product obtained in the invention may be separated and concentrated by the existing method, but it is possible to isolate the product only by a simple distillation since a para-substituted aromatic hydrocarbon with an extremely high purity is obtained selectively in the invention as previously mentioned. That is, it can be divided by the simple distillation into a fraction having a boiling point lower than that of the unreacted aromatic hydrocarbon, a high-purity para-substituted aromatic hydrocarbon and a fraction having a boiling point higher than that of the para-substituted aromatic hydrocarbon. When the amount of the fraction having a boiling point higher than that of the para-substituted aromatic hydrocarbon is extremely small, the high-purity para-substituted aromatic hydrocarbon can be isolated only by distilling off a light fraction. Moreover, the unreacted aromatic hydrocarbon may be recycled as a starting material.

[Methylation of Toluene]

Then, a particularly preferable embodiment of the invention, i.e. a case that the aromatic hydrocarbon is toluene and the para-substituted aromatic hydrocarbon is paraxylene will be described in detail. As the methylation reaction of toluene proceeds in the presence of the catalyst, it is assumed to form paraxylene as a target product as well as orthoxylene and methaxylene as a structural isomer, ethylbenzene, unreacted toluene, and alkylbenzens having a carbon number of 9 or more associated with the proceeding of methylation. In this case, the component ratio of paraxylene among aromatic hydrocarbons with a carbon number of 8 is preferable to become higher, and is preferably not less than 95 mol %, more preferably not less than 99.7 mol %, further preferably not less than 99.8 mol %, particularly not less than 99.9 mol % at the first stage of the reaction.

On the other hand, products other than the carbon number of 8 are preferable to become smaller. The residual amount of toluene having a carbon number of 7 is largely dependent upon the reaction temperature and the ratio of the methylating agent, but is preferably not more than 70 mol %, more preferably not more than 50 mol %, particularly not more than 30 mol % as a residual ratio assuming the actual process. When the residual ratio is high or when the conversion is low, it is required to return the unreacted toluene to the starting line for conducting the reaction again, and hence there is a demerit that the production efficient is largely lowered.

Since aromatic hydrocarbons having a carbon number of 9 or more are easily produced under the reaction condition that the ratio of the methylating agent becomes higher, it is preferable that the molar ratio of the methylating agent to toluene is not so high as previously mentioned. The content in total of the aromatic hydrocarbons having a carbon number of 9 or more in the reaction product is preferably not more than 5 mol %, more preferably not more than 1 mol %, particularly not more than 0.1 mol %. When the aromatic hydrocarbons having 9 or more substituents are large, a greater amount of energy is required for the separation such as distillation or the like, so that the content is particularly preferable to be not more than 0.1 mol %.

The reaction product may be separated and concentrated by the existing method, but it is possible to isolate the product only by a simple distillation since a para-substituted aromatic hydrocarbon with an extremely high purity is obtained selectively in the invention. That is, it can be divided by the simple distillation into a fraction having a boiling point lower than that of the unreacted toluene, a high-purity paraxylene and a fraction having a boiling point higher than that of paraxylene. When the amount of the fraction having a boiling point higher than that of paraxylene is extremely small, the high-purity paraxylene can be isolated only by distilling off a light fraction. Moreover, the unreacted toluene may be recycled as a starting material.

[Method of Producing Paraxylene]

Next, there will be described a method of producing paraxylene wherein both aromatic hydrocarbons with carbon numbers of 7 and 8 in the catalytic reformed oil can be utilized and paraxylene can be produced efficiently at a low cost by reducing a working ratio of isomerization-adsorption separation apparatus. The production method of paraxylene according to the invention is characterized by comprising a first step of producing paraxylene by methylation of an aromatic hydrocarbon, a second step of producing paraxylene by isomerization and/or adsorption separation of an aromatic hydrocarbon and a third step of mixing paraxylene obtained in the first step with paraxylene obtained in the second step. According to the production method of paraxylene of the invention, a high-purity paraxylene can be produced efficiently from an aromatic hydrocarbon by using the aforementioned catalyst. Also, paraxylene can be produced by the isomerization and/or adsorption separation, so that an aromatic hydrocarbon having a carbon number of 8 can be utilized as a starting material for paraxylene. In this case, paraxylene produced by the isomerization and/or adsorption separation is mixed with the high-purity paraxylene produced by the methylation of the aromatic hydrocarbon to provide a final product, whereby it is made possible to lower the purity of paraxylene produced by the isomerization and/or adsorption separation, and hence the working ratio of isomerization-adsorption separation apparatus can be reduced to reduce the production cost as a whole.

<First Step>

In the production method of paraxylene according to the invention, paraxylene is produced by reacting a methylating agent and an aromatic hydrocarbon in the presence of a catalyst formed by coating MFI type zeolite having a particle size of not more than 100 μm with a crystalline silicate at the first step. The first step in the production method of paraxylene according to the invention utilizes the aforementioned method of producing a para-substituted aromatic hydrocarbon, in which the para-substituted aromatic hydrocarbon as a target product is paraxylene.

<Second Step>

In the production method of paraxylene according to the invention, paraxylene is produced by isomerizing and/or adsorption separating an aromatic hydrocarbon having a carbon number of 8 at the second step. As the isomerization and/or adsorption separation method can be applied the conventionally known method. In this case, the starting aromatichydrocarbon having a carbon number of 8 includes orthoxylene, methaxylene, ethylbenzen and the like in addition to paraxylene. Moreover, as the starting aromatic hydrocarbon having a carbon number of 8 can be generally used a mixed xylene easily available from catalytic reformed oil, ethylene cracker, decomposed oil derived from coal or the like.

In the isomerization of the second step, orthoxylene and methaxylene in the starting material are isomerized to paraxylene. When ethylbenzene is included in the starting material, the isomerization may be carried out after the ethylbenzene is removed or ethylbenzene is deethylated by hydrogenation to convert into benzene and ethane or changed into xylene through naphthene. Moreover, the concentration of ethylbenzene in the starting material to be isomerized is preferably not more than 2 weight %, more preferably not more than 1 weight %. Also, the catalyst used for the isomerization reaction is not particularly limited, but an acid type zeolite is preferable, and MFI type zeolite is particularly preferable. The reaction system is preferable to be a fixed bed circulating reaction system, which may be a liquid phase or vapor phase. The liquid phase is preferable because the yield of the isomerization reaction is high, but it is required to take a way so as not to store ethylbenzene in the system because dealkylation of ethylbenzene is low.

In the adsorption separation of the second step, the starting materials are moved through an adsorbing tower filled with an adsorbent, during which paraxylene having an adsorbing force stronger than that of other isomers is adsorbed and separated from the other isomers. Then, paraxylene is drawn out from the system with a desorbing agent and desorbed and separated from a desorbing liquid by distillation. As the desorbing agent is preferably used a faujasite zeolite exchanged with potassium or barium ion. As an actual process are mentioned PAREX method by UOP and AROMAX method by Toray Industries, Inc. Moreover, either of the isomerization step and the adsorption separation step may be a previous step, but a recycle type is desirable instead of one-through type. That is, the concentrated extract (high-purity paraxylene) is separated from a raffinate (aromatic hydrocarbon fraction with a carbon number of 8 removing paraxylene) through the adsorption separation step. The separated raffinate is re-introduced into the isomerization step to convert into paraxylene, whereby the high-purity paraxylene can be produced efficiently.

<Third Step>

In the third step of the production method of paraxylene according to the invention, paraxylene obtained in the first step is mixed with paraxylene obtained in the second step. The mixing method is not particularly limited. Also, paraxylene obtained in the first step and paraxylene obtained in the second step are mixed at a proper ratio in accordance with a purity of paraxylene as a target product in the third step. The purity of paraxylene obtained in the third step is properly selected in accordance with applications and is preferably not less than 99.5 weight %, more preferably not less than 99.7 weight %.

In the production method of paraxylene comprising the first step, second step and third step according to the invention as mentioned above, paraxylene having an extremely high purity can be produced at the first step. Since the purity of paraxylene obtained in the first step is very high, even if the burden of the second step being high in the running cost is reduced to lower the purity of paraxylene, paraxylene obtained in the third step of mixing paraxylene of the first step with paraxylene of the second step can taain a target purity by properly adjusting the mixing ratio.

EXAMPLES

The following examples are given in illustration of the invention and are not intended as limitations thereof.

[Catalyst a and Catalyst B]

Colloidal silica (ST-S made by Nissan Chemical Industries, Ltd. 30 weight % of silica), aluminum nitrate, sodium hydroxide, tetrapropyl ammonium bromide (TPABr) and deionized water are mixed at a ratio of $SiO_2:Al_2O_3:Na_2O:TPABr:H_2O=3.5:0, 025:0,05:0, 5:120$ (molar ratio, silica source, alumina source and sodium source are molar ratio based on oxide), which are hydrothermally synthesized at 180° C. for 24 hours and then sintered at 550° C. for 5 hours to obtain ZSM-5 zeolite (catalyst A).

Next, a sol for the formation of silicalite membrane is prepared by using colloidal silica, tetrapropyl ammonium hydroxide (TPAOH), ethanol (ETOH) and deionized water at a ratio of $SiO_2:TPAOH:ETOH:H_2O=2:0.5:0.8:120$ (molar ratio), The sol for the formation of silicalite membrane is applied onto the whole surface of individual particles of ZSM-5 zeolite (catalyst A) and hydrothermally synthesized at 180° C. over 24 hours (coating treatment). After the coating treatment is further repeated, the sintering is conducted at 550° C. for 5 hours to obtain a catalyst B formed by coating the whole surfaces of particles of ZSM-5 zeolite with the silicalite membrane.

Figure 1:
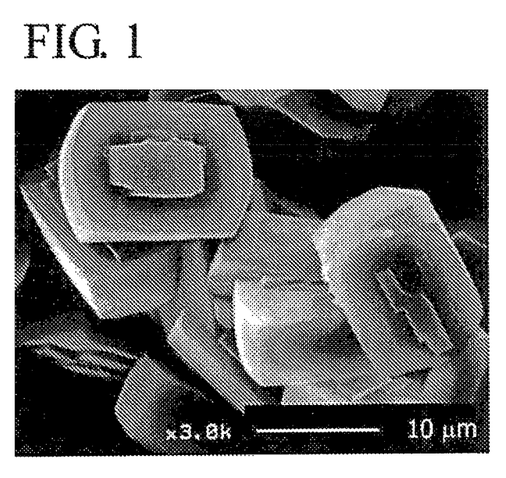
FIG. 1 is an SEM photograph of a catalyst A.
Figure 2:
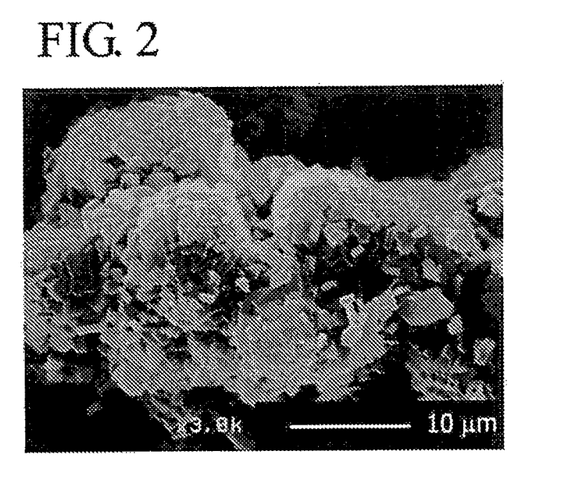
FIG. 2 is an SEM photograph of a catalyst B.
Figure 3:
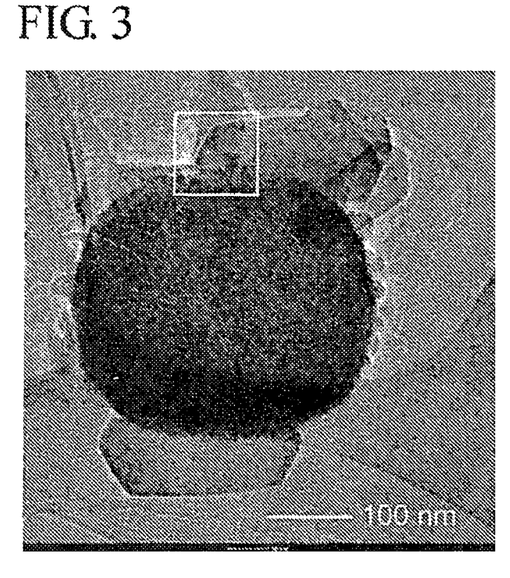
FIG. 3 is a TEM photograph of a catalyst B.
Figure 4:
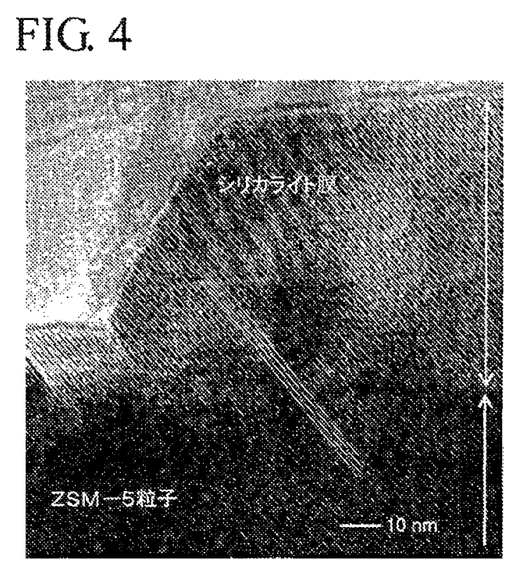
FIG. 4 is a TEM photograph of a catalyst B in the vicinity of an interface between ZSM-5 particles and silicalite membrane.

FIG. 1 is an SEM photograph of the catalyst A, which shown the formation of granular ZSM-5 catalyst having a particle size of about 10 μm. Also, FIG. 2 is an SEM photograph of the catalyst B, from which it is clear that the whole surface of the granular ZSM-5 catalyst is coated with the silicalite membrane. Moreover, the increment of weight by coating of silicalite is about 60 weight %. Further, FIG. 3 is a TEM photograph of the catalyst B and FIG. 4 is a TEM photograph of the vicinity of interface between ZSM-5 particles and silicalite membrane, from which it is clear that pores of ZSM-5 and pores of silicalite membrane have a continuity.

Examples A-1~A-2

In a fixed layer reaction vessel of 4 mm in inner diameter is filled 0.05 g of the catalyst B by diluting with glass beads of 1.0 mmϕ to form a catalyst layer having a length of 20 mm, and 0.82 mmol/hr of toluene, 0.82 mmol/hr (Example A-1) or 2.46 mmol/hr (Example A-2) of methanol and 17 ml/min of helium gas are supplied thereto to conduct alkylation reaction of toluene at 400° C. under an atmospheric pressure. After 1 hour and 3 hours from reaction start, a product at an outlet of the reaction vessel is analyzed through a gas chromatography to measure a ratio of isomers formed. The results are shown in Table 1, and the measuring conditions of the gas chromatography are shown below.

Measuring apparatus: GC-14A made by Shimadzu Corporation

Column: capillary column Xylene Master made by Shinwa Kako Co., Ltd. inner diameter 0.32 mm, 50 m Temperature condition: column temperature 50° C., temperature rising rate 2° C./min, detector (FID) temperature 250° C.

Carrier gas: helium

Toluene conversion(mol %)=100−(residual mol of toluene/mol of toluene in starting material)×100

Paraxylene selectivity(mol %)=(mol of paraxylene produced/mol of C8 aromatic hydrocarbon produced)×100

Activity residual ratio of stable stage to initial stage(%)= (toluene conversion after 3 hours from reaction start)/(toluene conversion after 1 hour from reaction start)×100

Examples A-3~A-4

The alkylation of toluene is carried out under the same conditions as in Examples A-1~A-2 except that the molar ratio of methanol/toluene is 0.4 (Example A-3) and 10.0 (Example A-4), respectively. The results are shown in Table 1.

Comparative Example A-1

The alkylation of toluene is carried out under the same conditions as in Example A-2 except that the catalyst A is used instead of the catalyst B. The results are shown in Table 1.

TABLE 1

|  |  | Example A-1 | Example A-2 | Example A-3 | Example A-4 | Comparative Example A-1 |
|---|---|---|---|---|---|---|
| catalyst |  | — | B | B | B | A |
| molar ratio of methanol/toluene | mol/mol | 1 | 3 | 0.4 | 10 | 3 |
| After 1 hour from reaction start |  |  |  |  |  |  |
| toluene conversion | mol % | 33.2 | 21.6 | 6.0 | 8.6 | 71.8 |
| paraxylene selectivity | mol % | not less than 99.9 | not less than 99.9 | not less than 99.9 | 76.3 | 42.4 |
| Composition of product oil |  |  |  |  |  |  |
| benzene | mol % | not more than 0.1 | not more than 0.1 | not more than 0.1 | not more than 0.1 | not more than 0.1 |

TABLE 1-continued

|  |  | Example A-1 | Example A-2 | Example A-3 | Example A-4 | Comparative Example A-1 |
|---|---|---|---|---|---|---|
| toluene | mol % | 66.8 | 78.4 | 94.0 | 91.4 | 28.2 |
| ethylbenzene | mol % | not more than 0.1 | not more than 0.1 | not more than 0.1 | not more than 0.1 | not more than 0.1 |
| paraxylene | mol % | 26.7 | 20.3 | 5.9 | 5.8 | 20.5 |
| methaxylene | mol % | not more than 0.1 | not more than 0.1 | not more than 0.1 | 1.2 | 15.6 |
| orthoxylene | mol % | not more than 0.1 | not more than 0.1 | not more than 0.1 | 0.6 | 12.2 |
| aromatic hydrocarbons having a carbon number of 9 or more | mol % | 6.5 | 1.3 | 0.1 | 1.0 | 23.5 |
| total | mol % | 100 | 100 | 100 | 100 | 100 |
|  |  | After 3 hours from reaction start | | | | |
| toluene conversion | mol % | 34.5 | 21.9 | 1.2 | 1.8 | 74.6 |
| paraxylene selectivity | mol % | not less than 99.9 | 99.3 | not less than 99.9 | 75.2 | 43.7 |
|  |  | Composition product oil | | | | |
| benzene | mol % | not more than 0.1 | not more than 0.1 | not more than 0.1 | not more than 0.1 | not more than 0.1 |
| toluene | mol % | 65.5 | 78.1 | 98.8 | 98.2 | 25.4 |
| ethylbenzene | mol % | not more than 0.1 | not more than 0.1 | not more than 0.1 | not more than 0.1 | not more than 0.1 |
| paraxylene | mol % | 28.0 | 20.5 | 1.2 | 1.0 | 21.5 |
| methaxylene | mol % | not more than 0.1 | not more than 0.1 | not more than 0.1 | 0.3 | 15.9 |
| orthoxylene | mol % | not more than 0.1 | not more than 0.1 | not more than 0.1 | 0.1 | 11.8 |
| aromatic hydrocarbons having a carbon number of 9 or more | mol % | 6.5 | 1.4 | not more than 0.1 | 0.4 | 25.4 |
| total | mol % | 100 | 100 | 100 | 100 | 100 |
| Activity residual ratio of stable stage to initial stage | % | 104 | 101 | 20 | 21 | 104 |

As seen from Examples A-1 to A-4, the selectivity of p-xylene can be considerably increased by using the catalyst coated with silicalite (catalyst B) as compared with a thermodynamically equilibrium composition (about 25%) to selectively produce p-xylene.

Also, it has been understood that when the molar ratio of methanol to toluene is 0.45~4.0 and the catalyst coated with silicalite (catalyst B) is used as described in Examples A-1 to A-2, the selectivity of p-xylene is as very high as not less than 99% as compared with a thermodynamically equilibrium composition (about 25%) and the toluene conversion is also high and hence p-xylene is selectively produced. Further, it has been understood that caulking resulting from methanol-methanol reaction is suppressed since the lowering of the toluene conversion after 3 hours from reaction start is small as compared with that after 1 hour from reaction start. Moreover, the product oil comprises starting toluene (boiling point 110° C.), paraxylene (boiling point 138° C.) and aromatic hydrocarbons having a carbon number of 9 or more (boiling point 165-176° C.), so that the high-purity paraxylene can be easily obtained by distillation.

On the other hand, it can be seen from the results of Example A-3 that when the molar ratio of methanol to toluene is less than 0.45, the toluene conversion is largely lowered as compared with the other examples and the deterioration of the activity is remarkable.

Furthermore, it can be seen from Example A-4 that when the molar ratio of methanol to toluene exceeds 4.0, the toluene conversion after the reaction start and after 3 hours are considerably lowered as compared with the other examples.

As seen from the results of Examples A-1 to A-4, when methanol is used as a methylating agent, the molar ratio of methanol to the aromatic hydrocarbon is preferable to be not less than 0.45 but not more than 4.0.

As seen from the results of Comparative Example A-1, when the catalyst A is used instead of the catalyst B, the paraxylene selectivity is considerably lowered as compared with the examples.

[Catalyst C, Catalyst D, Catalyst E and Catalyst F]

A catalyst C and a catalyst D are obtained by pressing the catalyst A and the catalyst B, respectively. Moreover, press forming conditions are a forming pressure of 8 tons and a holding time of 10 minutes. Further, a catalyst E and a catalyst F are obtained by sieving the catalyst C and the catalyst D to 16-24 meshes, respectively.

Example B-1

In a fixed layer reaction vessel of 4 mm in inner diameter is filled 0.05 g of the catalyst F to form a catalyst layer, and 0.82 mmol/hr of toluene, 3.28 mmol/hr of methanol and 17 ml/min of helium gas are supplied thereto to conduct methylation of toluene at 400° C. under an atmospheric pressure. After 1 hour and 5 hours from reaction start, a product at an outlet of the reaction vessel is analyzed through a gas chromatographyto measure a forming ratio of isomers. The results are shown in Table 2.

Activity residual ratio of stable stage to initial stage(%)=(toluene conversion after 5 hours from reaction start)/(toluene conversion after 1 hour from reaction start)×100

Example B-2 and Comparative Examples B-1 to B-2

The methylation of toluene is carried out under the sane conditions as in Example B-1 except that the catalyst E (Comparative Example B-1), catalyst B (Example B-2) and catalyst A (Comparative Example B-2) are used instead of the catalyst F, respectively. The results are shown in Table 2.

On the contrary, it can be seen from the results of Comparative Example B-1 that when the catalyst E is used instead of the catalyst F, the porosity is proper but the catalyst composition is not favorable and hence the selectivity of paraxylene is highly lowered as compared with Example B-1.

Further, it can be seen from the results of Comparative Example B-2 that when the catalyst A is used instead of the

TABLE 2

| | | Example B-1 | | Comparative Example B-1 | | Example B-2 | | Comparative Example B-2 | |
|---|---|---|---|---|---|---|---|---|---|
| catalyst | — | F | | E | | B | | A | |
| filling density of catalyst layer | g/ml | 0.534 | | 0.547 | | 0.602 | | 0.610 | |
| reaction time | hr | 1 | 5 | 1 | 5 | 1 | 5 | 1 | 5 |
| toluene conversion | mol % | 33.2 | 33.3 | 55.4 | 55.5 | 21.6 | 15.3 | 41.4 | 35.9 |
| paraxylene selectivity | mol % | not less than 99.9 | not less than 99.9 | 23.8 | 23.8 | not less than 99.9 | not less than 99.9 | 48.9 | 50.5 |
| Composition of product oil | | | | | | | | | |
| benzene | mol % | not more than 0.1 | not more than 0.1 | not more than 0.1 | not more than 0.1 | not more than 0.1 | not more than 0.1 | not more than 0.1 | not more than 0.1 |
| toluene | mol % | 66.8 | 66.7 | 44.6 | 44.5 | 78.4 | 84.7 | 58.6 | 64.1 |
| ethylbenzene | mol % | not more than 0.1 | not more than 0.1 | not more than 0.1 | not more than 0.1 | not more than 0.1 | not more than 0.1 | not more than 0.1 | not more than 0.1 |
| paraxylene | mol % | 26.7 | 26.4 | 10.1 | 10.0 | 20.3 | 14.1 | 15.2 | 13.9 |
| methaxylene | mol % | not more than 0.1 | not more than 0.1 | 22.7 | 22.5 | not more than 0.1 | not more than 0.1 | 6.7 | 5.8 |
| orthoxylene | mol % | not more than 0.1 | not more than 0.1 | 9.7 | 9.5 | not more than 0.1 | not more than 0.1 | 9.2 | 7.8 |
| aromatic hydrocarbons having a carbon number of 9 or more | mol % | 6.5 | 6.9 | 12.9 | 13.5 | 1.3 | 1.1 | 10.2 | 8.4 |
| total | mol % | 100 | 100 | 100 | 100 | 100 | 100 | 100 | 100 |
| Activity residual ratio of stable stage to initial stage | % | standard | 100 | standard | 100 | standard | 71 | standard | 87 |

As seen from Examples B-1 and B-2, the selectivity of p-xylene can be considerably increased by using the catalyst coated with silicalite (catalyst F or catalyst B) as compared with a thermodynamically equilibrium composition (about 25%) to selectively produce p-xylene.

Also, it can be seen that when the catalyst coated with silicalite is used and proper catalyst size is set to properly hold a porosity as described in Example B-1, the selectivity of p-xylene is as very high as not less than 99.9% while suppressing the deterioration of the catalyst activity due to the drift of the starting materials as compared with a thermodynamically equilibrium composition (about 25%), and hence p-xylene is produced selectively. Moreover, the product oil comprises starting toluene (boiling point 110° C.), paraxylene (boiling point 138° C.) and aromatic hydrocarbons having a carbon number of 9 or more (boiling point 165-176° C.), so that the high-purity paraxylene can be easily obtained by distillation.

Further, it can be seen from the results of Example B-2 that when the catalyst B is used instead of the catalyst F and the porosity is not held properly, the activity residual ratio of stable stage to initial stage is largely lowered as compared with Example B-1 and hence caulking is caused due to the methanol-methanol reaction.

As seen from the results of Examples B-1 and B-2, the catalyst filling density is preferable to be not less than 0.10 g/ml but not more than 0.60 g/ml.

catalyst F and the porosity is not held properly, the selectivity of paraxylene is highly lowered as compared with Example B-1 but also the activity residual ratio of stable stage to initial stage is largely lowered as compared with Example B-1 to cause caulking due to the methanol-methanol reaction.

Examples C-1 to C-5

In a fixed layer reaction vessel of 4 mm in inner diameter is filled 0.05 g of the catalyst B by diluting with glass beads of 1.0 mmϕ to form a catalyst layer having a length of 20 mm, and 1.37 mmol/hr of toluene, 5.36 mmol/hr of DME and 17 ml/min of helium gas are supplied thereto to conduct alkylation of toluene at 200-400° C. under an atmospheric pressure. After 1 hour from reaction start, a product at an outlet of the reaction vessel is analyzed through a gas chromatography to measure a forming ratio of isomers. The results are shown in Table 3.

Examples C-6 to C-8

Alkylation of toluene is carried out under the same conditions as in Examples C-3 ~C-5 except that methanol is used instead of DME as an alkylating agent. The results are shown in Table 4. Moreover, the amount of methanol supplied is 5.28 mmol/hr.

Comparative Examples C-1 to C-2

Alkylation of toluene is carried out under the same conditions as in Examples C-6 and C-8 except that the catalyst A is used instead of the catalyst B. The results are shown in Table 4.

TABLE 3

|  |  | Example C-1 | Example C-2 | Example C-3 | Example C-4 | Example C-5 |
|---|---|---|---|---|---|---|
| catalyst | — | B | B | B | B | B |
| reaction temperature | °C. | 200 | 250 | 300 | 350 | 400 |
| alkylating agent | — | DME | DME | DME | DME | DME |
| toluene conversion | mol % | 4 | 9 | 50 | 88 | 86 |
| paraxylene selectivity | mol % | not less than 99.9 | not less than 99.9 | not less than 99.9 | not less than 99.9 | not less than 99.9 |
| Composition of product oil |  |  |  |  |  |  |
| benzene | mol % | not more than 0.1 | not more than 0.1 | not more than 0.1 | not more than 0.1 | not more than 0.1 |
| toluene | mol % | 96 | 91 | 50 | 12 | 14 |
| ethylbeozene | mol % | not more than 0.1 | not more than 0.1 | not more than 0.1 | not more than 0.1 | not more than 0.1 |
| paraxylene | mol % | 2 | 6 | 39 | 56 | 58 |
| methaxylene | mol % | not more than 0.1 | not more than 0.1 | not more than 0.1 | not more than 0.1 | not more than 0.1 |
| orthoxylene | mol % | not more than 0.1 | not more than 0.1 | not more than 0.1 | not more than 0.1 | not more than 0.1 |
| aromatic hydrocarbons having a carbon number of 9 or more | mol % | 2 | 3 | 11 | 32 | 28 |
| total | mol % | 100 | 100 | 100 | 100 | 100 |

TABLE 4

|  |  | Example C-6 | Example C-7 | Example C-8 | Comparative Example C-1 | Comparative Example C-2 |
|---|---|---|---|---|---|---|
| catalyst | — | B | B | B | A | A |
| reaction temperature | °C. | 300 | 350 | 400 | 300 | 400 |
| alkylating agent | — | methanol | methanol | methanol | methanol | methanol |
| toluene conversion | mol % | 1 | 4 | 27 | 39 | 72 |
| paraxylene selectivity | mol % | not less than 99.9 | not less than 99.9 | not less than 99.9 | 48 | 42 |
| Composition of product oil |  |  |  |  |  |  |
| benzene | mol % | not more than 0.1 | not more than 0.1 | not more than 0.1 | not more than 0.1 | not more than 0.1 |
| toluene | mol % | 99 | 96 | 73 | 61 | 28 |
| ethyl benzene | mol % | not more than 0.1 | not more than 0.1 | not more than 0.1 | not more than 0.1 | not more than 0.1 |
| paraxylene | mol % | 0.5 | 3 | 21 | 14 | 21 |
| methaxylene | mol % | not more than 0.1 | not more than 0.1 | not more than 0.1 | 6 | 16 |
| orthoxylene | mol % | not more than 0.1 | not more than 0.1 | not more than 0.1 | 9 | 12 |
| aromatic hydrocarbons having a carbon number of 9 or more | mol % | 0.5 | 1 | 6 | 10 | 23 |
| total | mol % | 100 | 100 | 100 | 100 | 100 |

As seen from Examples C-1 to C-8, the selectivity of p-xylene can be considerably increased by using the catalyst coated with silicalite (catalyst B) as compared with a thermodynamically equilibrium composition (about 25%) to selectively produce p-xylene.

Also, it can be seen that when DME is used as an alkylating agent and the catalyst coated with silicalite (catalyst B) is used as described in Examples C-1 to C-5, the selectivity of p-xylene is as very high as not less than 99.9% as compared with a thermodynamically equilibrium composition (about 25%) and also the toluene conversion is high, and hence p-xylene is produced selectively. Moreover, the product oil comprises starting toluene (boiling point 110° C.), paraxylene (boiling point 138° C.) and aromatic hydrocarbons having a carbon number of 9 or more (boiling point 165-176° C.), so that the high-purity paraxylene can be easily obtained by distillation.

On the other hand, it can be seen from the results of Examples C-6 to C-8 that when methanol is used as the alkylating agent, the toluene conversion is highly lowered as compared with Examples C-1 to C-5.

As seen from the results of Examples C-1 to C-8, DME is particularly excellent as a methylating agent.

As seen from the results of Comparative Examples C-1 to C-2, when methanol is used as an alkylating agent and the catalyst A is used instead of the catalyst B, the selectivity of paraxylene is largely lowered as compared with Examples C-1 to C-8.

Examples D-1 to D-2

<Methylation of Toluene>

In a fixed layer reaction vessel of 4 mm in inner diameter is filled 0.05 g of the catalyst B by diluting with glass beads of 1.0 mmφ to form a catalyst layer having a length of 20 mm, and 0.82 mmol/hr of toluene, 3.28 mmol/hr of methanol (Example D-1) or 5.36 mmol/hr of dimethyl ether (DME) (Example D-2) and 17 ml/min of helium gas are supplied thereto to conduct methylation of toluene at 400° C. under an atmospheric pressure. After 1 hour from reaction start, a product at an outlet of the reaction vessel is analyzed through a gas chromatography to measure a forming ratio of isomers. The results are shown in Table 5.

<Isomerization and Adsorption Separation of Aromatic Hydrocarbon with a Carbon Number of 8>

The adsorption separation is carried out using a mixed xylene obtained from a catalytic reformed oil as a starting material. The adsorption separation is conducted at 1 MPa and 180° C. by using ADS-7 made by UOP as an adsorbent and D-1000 made by UOP as a desorbing agent. Table 6 shows the thus obtained extract (high-purity paraxylene), raffinate (fraction of aromatic hydrocarbons with a carbon number of 8 removing paraxylene) and the starting mixed xylene. Further, the isomerization is carried out by using the raffinate obtained from the adsorption separation step as a starting material. The reaction is conducted at 1.5 MPa and 380° C. using an Isolene catalyst made by Toray Industries, Incorporation as a catalyst. The thus isomerized product oil is shown in Table 6. Moreover, the isomerized product oil is again mixed with the mixed xylene and introduced into the adsorption separation step for recycling to a step of producing paraxylene.

<Mixing Step>

The reaction product oil obtained in the first step is distilled to obtain 99.9 weight % of paraxylene. 100 parts by weight of paraxylene obtained in the first step is mixed with 9 parts by weight of 97.0 weight % of paraxylene obtained in the second step to obtain 99.7 weight % of paraxylene.

Comparative Example D-1

The disproportionation of toluene is carried out under the same conditions as in Example D-1 except that the catalyst A is used and 0.82 mmol/hr of toluene and 17 ml/min of helium gas are supplied without methanol and contacted at 2 MPaG. The results are shown in Table 5.

Comparative Example D-2

The methylation of toluene is carried out under the same conditions as in Example D-1 except that the catalyst A is used instead of the catalyst B.

TABLE 5

|  |  | Example D-1 | Example D-2 | Comparative Example D-1 | Comparative Example D-2 |
|---|---|---|---|---|---|
| catalyst |  | B | B | A | A |
| alkylating agent |  | methanol | DME | — | methanol |
| toluene conversion | mol % | 33.2 | 86.0 | 38.8 | 71.8 |
| paraxylene selectivity | mol % | not less than 99.9 | not less than 99.9 | 54.0 | 42.4 |
| Composition of product oil ||||||
| benzene | mol % | not more than 0.1 | not more than 0.1 | 18.7 | not more than 0.1 |
| toluene | mol % | 66.8 | 14.0 | 61.2 | 28.2 |
| etbylbenzene | mol % | not more than 0.1 | not more than 0.1 | 0.7 | not more than 0.1 |
| paraxylene | mol % | 26.7 | 58.0 | 10.1 | 20.5 |
| methaxylene | mol % | not more than 0.1 | not more than 0.1 | 7.2 | 15.6 |
| orthoxylene | mol % | not more than 0.1 | not more than 0.1 | 1.4 | 12.2 |
| aromatic hydrocarbons having a carbon number of 9 or more | mol % | 6.5 | 28.0 | 0.7 | 23.5 |
| total | mol % | 100 | 100 | 100 | 100 |

TABLE 6

|  |  | Adsorption separation ||| Isomerization ||
|---|---|---|---|---|---|---|
|  |  | starting material | extract | raffinate | starting material | product oil |
| Composition of product oil |||||||
| benzene | mol % | 0 | 0 | 0 | 0 | 1.2 |
| toluene | mol % | 1.6 | 2.8 | 1.2 | 1.2 | 2.9 |
| ethylbenzene | mol % | 0.3 | 0.1 | 0.4 | 0.4 | 0.5 |
| paraxylene | mol % | 22.9 | 97.0 | 1.1 | 1.1 | 36.9 |
| methaxylene | mol % | 51.5 | 0.1 | 66.6 | 66.6 | 41.2 |
| orthoxylene | mol % | 23.7 | 0 | 30.7 | 30.7 | 12.9 |
| aromatic hydrocarbons having a carbon number of 9 or more | mol % | 0 | 0 | 0 | 0 | 4.4 |
| total | mol % | 100 | 100 | 100 | 100 | 100 |

As described in Examples D-1 and D-2, when the methylation reaction of toluene is conducted by using a catalyst coated with silicalite (catalyst B), it can be seen that although the reaction is carried out under an atmospheric pressure, the selectivity of p-xylene is as very high as not less than 99.9% as compared with a thermodynamically equilibrium composition (about 25%) to selectively produce p-xylene.

on the other hand, it can be seen from the results of Comparative Example D-1 that when the disproportionation of toluene is conducted using the catalyst A, the selectivity of paraxylene is low.

Also, it can be seen from the results of Comparative Example D-2 that when the catalyst A is sued instead of the catalyst B, the selectivity of paraxylene is largely lowered as compared with the examples.

As seen from the above results, since the purity of paraxylene obtained by the methylation of toluene in Example D-1 is very high as compared with the comparative example, even if paraxylene having a relatively low purity is produced by the isomerization and/or adsorption separation requiring a significant quantity of energy consumption, the target purity can be attained by adjusting the mixing ratio properly.

The invention claimed is:

1. A method of producing a para-substituted aromatic hydrocarbon, the method comprising:
    reacting a methylating agent and an aromatic hydrocarbon in the presence of a catalyst formed by coating MFI type zeolite having a particle size of not more than 100 μm with a crystalline silicate to produce the para-substituted aromatic hydrocarbon.

2. A method of producing a para-substituted aromatic hydrocarbon according to claim 1, wherein the methylating agent is at least one selected from the group consisting of methanol and dimethyl ether.

3. A method of producing a para-substituted aromatic hydrocarbon according to claim 1, wherein a conversion of the aromatic hydrocarbon is not less than 30 mol% and paraxylene among aromatic hydrocarbons with a carbon number of 8 included in a reaction product is not less than 95 mol %.

4. A method of producing a para-substituted aromatic hydrocarbon according to claim 1, wherein a para-substituted aromatic hydrocarbon with a high purity is obtained from a reaction product by distillation without isomerization-adsorption separation.

5. A method of producing paraxylene, comprising:
    a step of providing an aromatic hydrocarbon for the following first step and aromatic hydrocarbons with a carbon number of 8 for the following second step;
    the first step of reacting a methylating agent and the aromatic hydrocarbon in the presence of a catalyst formed by coating MFI type zeolite having a particle size of not more than 100 μm with a crystalline silicate to produce paraxylene;
    the second step of isomerizing and/or adsorption separating the aromatic hydrocarbons with a carbon number of 8 to produce paraxylene; and
    a third step of mixing paraxylene obtained in the first step with paraxylene obtained in the second step.

* * * * *